United States Patent [19]

Fujimoto

[11] Patent Number: 5,263,923
[45] Date of Patent: Nov. 23, 1993

[54] WEARING ARTICLE FOR WEARING IN PRESSED RELATION TO HUMAN BODY SURFACE

[75] Inventor: Masami Fujimoto, Kyoto, Japan
[73] Assignee: Wacoal Corp., Kyoto, Japan
[21] Appl. No.: 762,980
[22] Filed: Sep. 20, 1991

[30] Foreign Application Priority Data

May 22, 1991 [JP] Japan .................................. 3-147873

[51] Int. Cl.$^5$ ............................................ A61F 13/00
[52] U.S. Cl. ........................................ 602/62; 602/63
[58] Field of Search ............... 128/155, 157, 165, 169; 602/60–66, 75, 76, 77; 2/16, 22, 59, DIG. 7

[56] References Cited

U.S. PATENT DOCUMENTS

| | | | |
|---|---|---|---|
| 1,544,641 | 7/1925 | Guinzburg | 602/63 |
| 3,683,904 | 8/1972 | Forster | 128/127 |
| 3,945,046 | 3/1976 | Stromgren | 602/63 |
| 3,949,750 | 4/1976 | Freeman | 128/260 |
| 4,065,814 | 1/1978 | Fox | 2/79 |
| 4,461,295 | 7/1984 | Herrick | 128/303.1 |
| 4,492,227 | 1/1985 | Senn et al. | 602/63 |
| 4,650,851 | 3/1987 | Rhum et al. | 528/354 |
| 4,660,546 | 4/1987 | Herrick | 128/1 |

OTHER PUBLICATIONS

Watanuki et al, "The Effect of Partial Pressure on Upper Extremity upon Skin Temperature and Electromyogram", Annals Physiol. Antrop. 6(2): 69–74, 1987.
Watanuki et al, "The Effect of Partial Pressure on Lower Extremity upon Skin Temperature and Electromyogram", Annals Physiol. Anthrop. 6(2): 75–82, 1987.
The Punctum Plug: Evaluation of a New Treatment for Dry Eye; Freeman; American Academy of Ophthalomology and Optometry, pp. OP-874 through OP-879, vol. 79 Nov.–Dec. 1975.
Diagnosis and Treatment of Keroconjunctivitis, New Orleans, Barraquer et al, Acad. of Ophthalmology, 1980, p. 43.
Intra–Canilicular Gelatin Implants in the Treatment of Kerato–Conjunctivitis Sicca by Wallace S. Foulds; Brit; J. Ophthal (1961) vol. 45, pp. 625–627.
Blinking and the Mechanics of the Lacrimar Drainage System; Marshall G. Doane, Ophthalmology, vol. 88, No. 8, Aug. 1981, pp. 844 through 851.
Lacrimal Function, Jones L. T.; Marquis M. M.; and Vincent H. J.; American Journal Ophthalmol 73; 1972, pp. 658–659.

Primary Examiner—Randy C. Shay
Attorney, Agent, or Firm—Armstrong, Westerman, Hattori, McLeland & Naughton

[57] ABSTRACT

A wearing article with a tapering function for wearing on a human body in pressed relation to a surface of the human body, has a heavily-stretchable portion which has an excellent tightening force and is adapted to be held against a required portion of the human body so as to extend generally along muscle fibers over a region from a tendon to a central portion of the muscle. The remainder of the wearing article is defined by an easily-stretchable portion. With this arrangement, by merely wearing this wearing article on the required portion of the body, the heavily-stretchable portion tightens only a required portion of the body to support the central portion of the relevant muscle, thereby easily achieving a taping function.

7 Claims, 4 Drawing Sheets

WEARING ARTICLE FOR WEARING IN PRESSED RELATION TO HUMAN BODY SURFACE

BACKGROUND OF THE INVENTION

This invention relates to wearing articles or clothes with a taping function which are adapted to be worn on and tightly fitted on various parts of the human body so as to reinforce the relevant articulations (joints) and muscles.

When participating in various types of sport activities and trainings, or taking part in various kinds of exercise for fitness purposes, people put on the type of wearing articles which prevent an external wound and prevent the relapse of a wound. In addition, in order to effectively prevent an injury and to provide an effective remedy, there has been widely used a so-called taping treatment in which a suitable length of tape of an elastic nature or a nonelastic nature is tightly wound on or adhesively bonded tightly to the articulation, the muscle or the ligament of the human body. Namely, the taping treatment is used to prevent an injury, a wound resulting from fatigue, the relapse of such wound, or to provide an emergency treatment at the site immediately after an accident. After the injury is healed, the taping is used for reinforcing the healed portion. Originally, the taping is intended to reinforce the articulation and the muscle, using a medical or an athletic adhesive tape having an acrylic resin adhesive coated on one surface of a substrate of cotton or polyester, and this tape is adapted to be tightly wound on or adhesively bonded to a required portion of the human body so as to prevent an injury, to provide an emergency treatment, to promote rehabilitation and to prevent the relapse of an injury.

Besides such taping, there have been widely used supporters which are made of an elastic material and adapted to be put on a portion of the human body, such as an ankle and a knee.

However, when the tape is to be applied to a required portion of the human body, much skill is needed for such taping treatment. If the tape is not applied properly (for example, the application of the tape to an improper portion, or by an unskillful and inadequate taping), not only is the intended purpose (i.e., the prevention of an injury and a remedy) is achieved, but also this adversely affects various kinds of exercise, which may result in the interruption in blood circulation and a nerval trouble, and besides this tends to adversely affect the muscle. Therefore, it is necessary that the tape should be applied by those who have acquired a taping technique, and unskilled persons can not easily apply the tape.

When a supporter is to be used, a suitable supporter of a configuration corresponding to a required portion of the human body is chosen, and it can be quite easily attached to the required portion. However, although the supporter can provide a support in a direction perpendicular to the human body surface, it can not provide a required support force in a direction inclined relative to the human body surface, or in a spiral direction, or in a direction along the human body surface, so that a sufficient support can not be achieved because of an insufficient tightening force. Namely, such a supporter merely applies a pressure to the human body, but can not function to limit the movement of the relevant portion of the human body. Particularly when a force is applied to the abdominal muscle or the like, the muscle is expanded and contracted, and therefore the muscle is expanded to increase its diameter. Therefore, when a force is applied to the human body surface in perpendicular relation thereto, the expansion and contraction of the muscle are prevented, and fatigue is not alleviated, and in contrast this causes a muscle fatigue.

In addition to the above-mentioned drawbacks of the prior art methods, another disadvantage has been encountered with the above taping and the above supporters. More specifically, that portion of the human body surface to which the taping or the supporter is applied is subjected to a tightening force, and therefore the difference between said that surface and the other surface portions appears because of the pressure difference, so that an unnatural step and profile can be recognized from the external appearance. This is quite unsightly, and particularly in the case of women, whose silhouette can not be kept beautiful.

SUMMARY OF THE INVENTION

According to the present invention, there is provided a wearing article with a taping function for wearing on a human body in pressed relation to a surface of the human body, comprising at least one heavily-stretchable portion which has an excellent tightening force and is adapted to be held against a required portion of the human body so as to extend generally along muscle fibers over a region from a tendon to a central portion of the muscle; the remainder of the wearing article being defined by an easily-stretchable portion.

The heavily-stretchable portion is pressed against that portion (e.g. muscle or articulation) of the human body requiring a taping treatment, in such a manner that the heavily-stretchable portion is extended along the muscle fibers over the region from the tendon to the central portion of the muscle. The other portions not requiring such a taping treatment are covered by the easily-stretchable portion.

With this construction, the wearing article, when worn on the human body, has the portion applying a high tightening force to the body surface, and the portion applying a low tightening force to the body surface. The former portion applying the high tightening force achieves a localized tightening effect similar to that achieved with a taping treatment, thereby enabling the prevention and remedy of an injury. The wearing article can be provided in the form of a tights for the lower half of the human body, a sock, an overall tights, a limb supporter, a shoulder supporter, a glove and so on. Therefore, upon wearing of this wearing article, even those who are not skillful in the taping technique can obtain an effect similar to that of a taping treatment. The other portion of the integral wearing article except for the taping portion is made of a two-way stretchable material which can stretch longitudinally and transversely, and therefore the taping portion can not be recognized from an external view, and the wearing article can be smoothly worn on the body with a beautiful silhouette.

DESCRIPTION OF THE PREFERRED EMBODIMENTS

Wearing articles or clothes with a taping function according to preferred embodiments of the present invention, which are adapted to be worn on the human body in pressed relation to the human body surface, will now be described with reference to the drawings.

Figure 1:
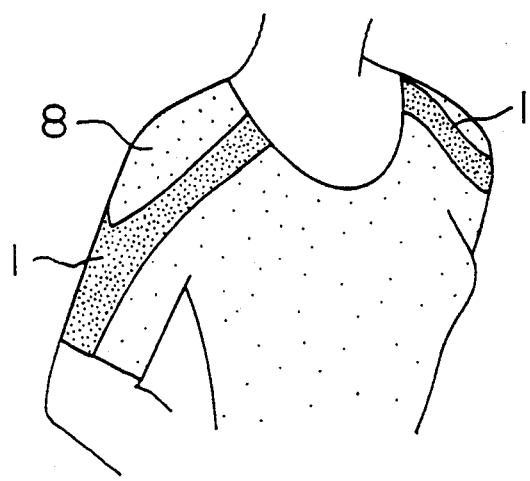
FIG. 1 is a perspective view of a shirt according to a preferred embodiment of the invention in which heavily-stretchable cloth pieces are provided so as to be disposed on the shoulders and the upper arm portions.
Figure 2:
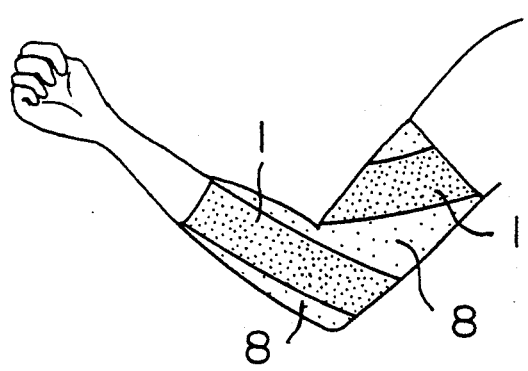
FIG. 2 is a side-elevational view of an elbow supporter according to another embodiment of the invention in which a heavily-stretchable cloth piece is provided so as to be disposed on the upper arm portion and the front arm portion.
Figure 3:
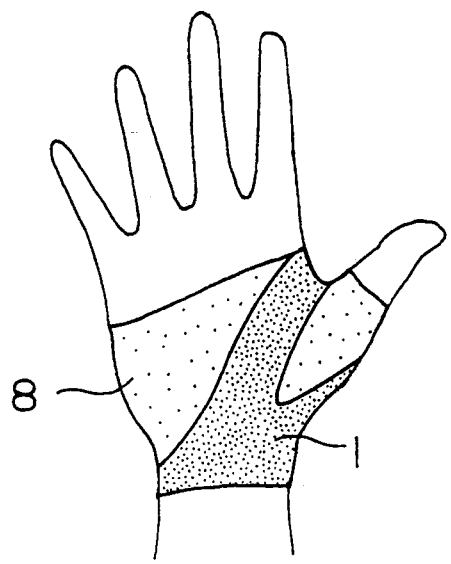
FIG. 3 is a front-elevational view of a glove according to a further embodiment of the invention in which a heavily-stretchable cloth piece is provided so as to be disposed on the back of the hand, the palm and the wrist.
Figure 4:
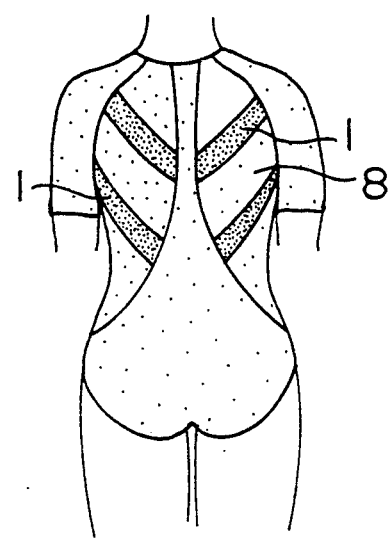
FIG. 4 is a rear view of a body wear according to a further embodiment of the invention in which heavily-stretchable cloth pieces are provided so as to be disposed on the back of the human body.
Figure 5:
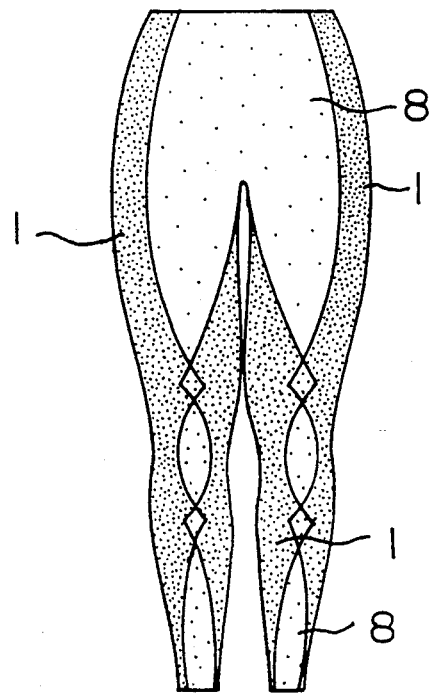
FIG. 5 is a front-elevational view of a long girdle according to a further embodiment of the invention in which a heavily-stretchable cloth piece is provided so as to be disposed on the thighs and the lower leg portions.
Figure 6:
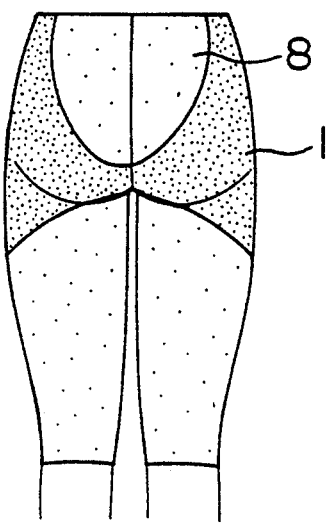
FIG. 6 is a rear view of a long girdle according to a further embodiment of the invention in which a heavily-stretchable cloth piece is provided so as to be disposed on the hips.
Figure 7:
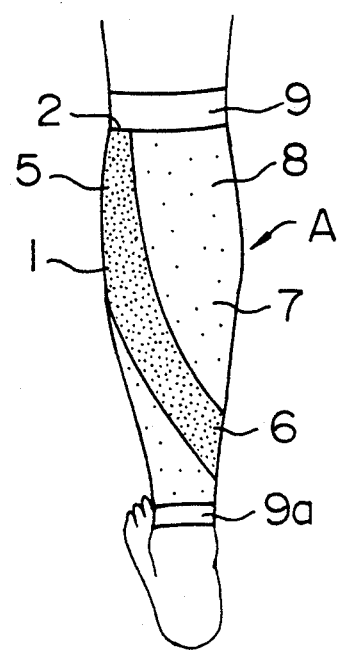
FIG. 7 is a rear view of a lower leg supporter according to a further embodiment of the invention in which a heavily-stretchable cloth piece is provided so as to be disposed on the lower leg portion.
Figure 8:
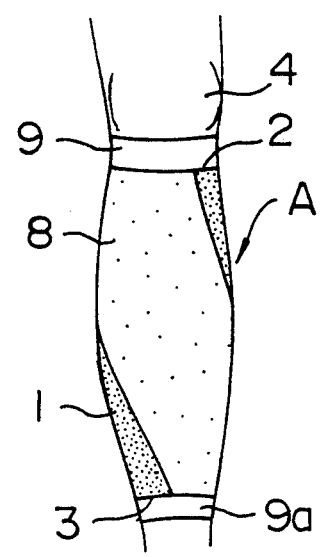
FIG. 8 is a front-elevational view of the lower leg supporter of FIG. 7.
Figure 9:
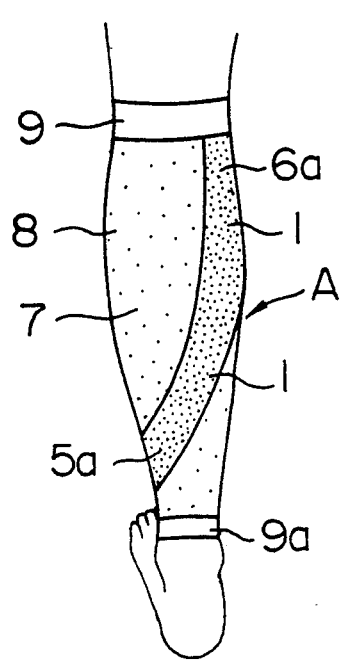
FIG. 9 is a rear view of a modified lower leg supporter.
Figure 10:
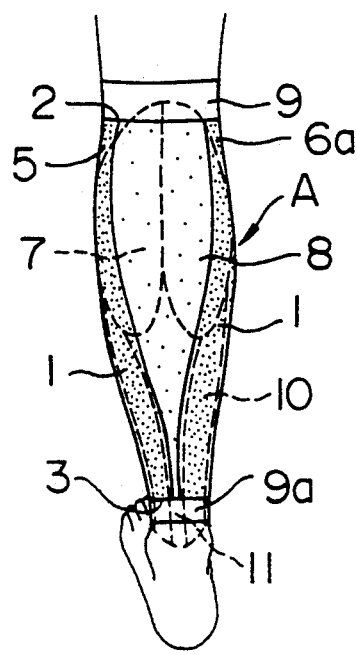
FIG. 10 a rear view of another modified lower leg supporter.

FIGS. 1 to 10 show various goods or articles embodying the present invention. FIG. 1 shows a shirt in which a heavily-stretchable cloth piece is provided so as to extend from each shoulder to the upper arm portion to provide a taping function. FIG. 2 shows an elbow supporter in which heavily-stretchable cloth pieces are provided so as to be disposed respectively at the upper arm portion and the front arm portion to provide a taping function. FIG. 3 shows a glove in which a heavily-stretchable cloth piece is provided so as to extend along the back of the hand and the palm and also to surround the wrist to provide a taping function. FIG. 4 shows a body wear in which heavily-stretchable cloth pieces are provided so as to hold the latissimus dorsi of the back of the human body and so on to provide a taping function. FIG. 5 shows a long girdle in which a heavily-stretchable cloth piece 1 for providing a taping function is provided so as to cover all of the front side of the lower half of the human body except for the front sides of the thighs, the knees and the front sides of the lower leg portions. FIG. 6 shows a long girdle in which a heavily-stretchable cloth piece 1 is provided so as to hold the gluteus maximus muscles and etc., of the hips to provide a taping function. FIG. 7 shows a lower leg supporter in which a heavily-stretchable cloth piece 1 is provided so as to hold the Achilles' tendon, the soleus, the gastrocnemius and etc., to provide a taping function. FIG. 8 is a front-elevational view of the lower leg supporter of FIG. 7. FIG. 9 is a rear-elevational view of a modified lower leg supporter. FIG. 10 shows another modified lower leg supporter in which heavily-stretchable cloth pieces 1 are provided to extend from the Achilles' tendon via the opposite side portions of the gastrocnemius toward the knee. In any of these wearing articles, the heavily-stretchable cloth piece 1 is provided linearly, slantingly or spirally (or in other suitable form) generally along the muscle fibers, so that the heavily-stretchable cloth piece can be pressed against the relevant portion of the human body surface.

Although the prevent invention can, of course, be applied to other forms of wearing articles than the above-mentioned articles, the lower leg supports (particularly, those in which the heavily-stretchable cloth piece is provided to extend from the Achilles' tendon via the opposite side portions of the gastrocnemius toward the knee) are mainly described specifically here for the sake of convenience.

Each of the supporters A shown in FIGS. 7 to 10 has a tubular shape, and is made of elastic (stretchable) materials (e.g. a spandex) sewn together. The supporter A fits on the lower leg to extend between the knee and the ankle so as to tighten this portion. The predetermined portion of the supporter A is lined with the heavily-stretchable cloth piece 1 in the form of a band. With this arrangement, when the supporter A is worn on the lower leg, the heavily-stretchable portion (where the heavily-stretchable cloth piece 1 is provided is pressed against the human body surface with a higher tightening force so as to provide a taping function, whereas the other portion of the supporter A (that is, an easily-stretchable cloth 8) is pressed against the human body surface with a lower tightening force. Thus, the supporter A has the two portions having different stretching (elastic) characteristics, respectively.

The heavily-stretchable cloth piece 1 is in the form of a band (360 denier×210 denier) having a generally uniform width, for example, of 4 to 6 cm throughout its length, and is made of a heavily-stretchable material, such as a spandex, which can be stretched longitudinally with a relatively high force. The supporter A is lined with the band-like heavily-stretchable cloth piece 1 by sewing, so that this cloth piece 1 is integrally connected to the supporter A. In the supporter A shown in FIG. 10, one of the heavily-stretchable cloth pieces 1 extends downward from the upper portion 5 of the outer side of the lower leg (which is disposed slightly below the knee 4) toward the ankle obliquely to approach the center line of the rear side of the lower leg in such a manner that this heavily-stretchable cloth piece 1 is pressed against the upper outer portion of the gastrocnemius, part of the soleus and part of the Achilles' tendon. Reference numeral 2 denotes the upper end of this heavily-stretchable cloth piece 1, and reference numeral denotes the lower end thereof. The other heavily-stretchable cloth 1 extends downward from the upper portion 6a of the inner side of the lower leg (which is disposed slightly below the knee 4) toward the ankle obliquely to approach the center line of the rear side of the lower leg in such a manner that this heavily-stretchable cloth piece 1 is pressed against the upper inner portion of the gastrocnemius, part of the soleus and part of the Achilles' tendon. In the supporter A shown in FIG. 10, although the two separate heavily-stretchable cloth pieces 1 are used, they may be replaced by a single heavily-stretchable cloth piece which is branched or bifurcated right and left at a position above the Achilles' tendon.

In the lower leg supporter A shown in FIGS. 7 and 8, the heavily-stretchable cloth piece 1 extends spirally downward from the upper portion 5 of the outer side of the lower leg (which is disposed slightly below the knee 4) toward the ankle via the upper outer portion of the gastrocnemius of the calf 7 of the rear side of the lower leg. Reference numeral 2 denotes the upper end of this heavily-stretchable cloth piece 1, and reference numeral 3 denotes the lower end thereof. In the lower leg supporter A shown in FIG. 9, the heavily-stretchable cloth piece 1 extends spirally in a direction opposite to that shown in FIGS. 7 and 8. More specifically, the heavily-stretchable cloth piece 1 extends spirally downward form the upper portion 6a of the inner side of the lower leg (which is disposed slightly below the knee 4) toward the ankle via the upper inner portion of the gastrocnemius of the calf 7 of the rear side of the lower leg. Reference numeral 5[a denotes the lower portion o the outer side of the lower leg.

In the above supporters A, the heavily-stretchable cloth piece 1 attached to the inner side thereof provides a higher tightening force than the other portion (that is, the easily-stretchable cloth 8) of the supporter A, and therefore the heavily-stretchable cloth piece 1 can provide strong stretching characteristics almost the same as achieved with a taping treatment. When the band-like heavily-stretchable cloth piece 1 has a very much stronger stretching force than the easily-stretchable cloth 8, a taping treatment for achieving a stronger support effect can be provided. More specifically, the heavily-stretchable cloth piece 1 is stretched or expanded, and then in this condition this cloth piece 1 is sewn to the easily-stretchable cloth 8. With this arrangement, when the supporter A is worn on the lower leg, the heavily-stretchable cloth piece 1 is stretched, and therefore the heavily-stretchable cloth piece 1 tends to contract, so that a strong contracting force is applied in the direction of the muscle fibers.

As described above, in the supporters A of the embodiments of the present invention, the band-like heavily-stretchable cloth piece 1, having the uniform width throughout its length, is spirally provided. In other wearing articles to be worn on a required portion of the human body in pressed relation to the human body surface, the heavily-stretchable cloth piece 1 of a required shape is adapted to be provided on a required articulation or muscle so as to extend generally in the direction of the muscle fibers from the tendon to the central portion of the muscle. By doing so, the taping function can be achieved. The heavily-stretchable cloth piece 1 is applied to the human body surface along the muscle fibers, and is applied under pressure to part or the whole of the muscle fibers. The heavily-stretchable cloth piece 1 need only to be extended longitudinally in the direction of the muscle fibers. If, however, the heavily-stretchable cloth piece 1 is provided to surround the periphery of the human body or the lower leg in a plane perpendicular to a longitudinal direction of the lower leg and hence the heavily-stretchable cloth piece 1 applies pressure to the muscle from the periphery thereof perpendicularly toward the radially inner part of the muscle. If, however, the heavily-stretchable cloth piece 1 is provided, the muscle fatigue can not be alleviated, and also a remedy for an injury can not be achieved. In other words, the dissipation of the energy and the accumulation of a fatigue substance (e.g. lactic acid) cause the muscle fatigue. The recovery from the fatigue can be promoted by promoting the flow of the blood and the lymph to rapidly remove the fatigue substance. When the skin is subjected to a massage effect by applying a proper degree of pressure thereto, the flow of the blood and the lymph can be promoted, and the recovery from the fatigue can be promoted. However, when the muscular strength is exerted, the muscle fibers are contracted, and the muscle bundle becomes thicker, and it is not desirable to hold the central portion of the muscle (i.e., the thickened muscle bundle). In view of these, the above construction of the present invention is needed.

In the above embodiments, although the heavily-stretchable cloth piece 1 is integrally sewn to the supporter A by lining, the present invention is not limited to such arrangement. For example, there can be adopted a mold knitting method by which a heavily-stretchable portion and an easily-stretchable portion are provided in a supporter, a molding method by which a heavily-stretchable portion and an easily-stretchable portion is provided in a supporter while providing a three-dimensional configuration, a method in which the heavily-stretchable cloth piece 1 is sewn to the outer side of the supporter, and a method in which instead of the heavily-stretchable cloth piece 1, a coating of a synthetic resin is applied to the supporter to prevent the stretching.

Preferably, fastening bands 9 and 9a of a tubular shape are attached respectively to the upper and lower ends 2 and 3 of the supporter A so as to prevent the supporter A from becoming displaced out of place upwardly and downwardly. This arrangement provides another advantage that the upper and lower fastening bands 9 and 9a pull the supporter A in opposite directions, so that the taping function of the heavily-stretchable cloth piece 1 is enhanced. However, if the upper and lower ends 2 and 3 are sufficiently heavily stretchable, the use of fastening bands 9 and 9a may be omitted. Further, the above lower leg supporters may be modified into a leggin-type supporter in which a narrow strip is extended across the plantar arch.

Figure 11:
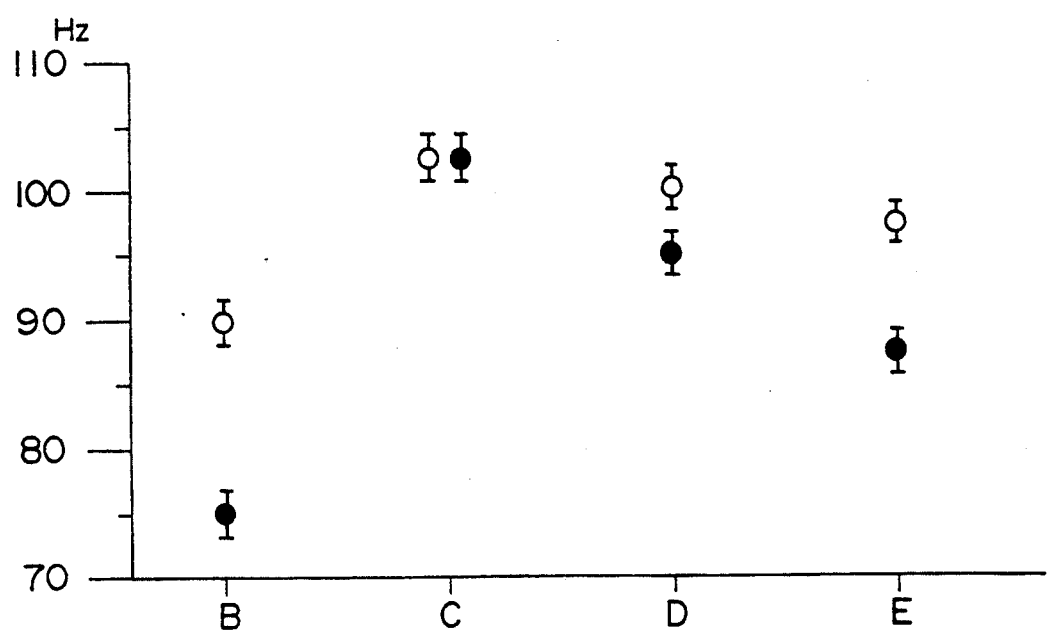
FIG. 11 is a graph showing results of muscle fatigue tests.

FIG. 11 shows results of muscle fatigue tests with respect to the lower leg supporter of the present invention. In the test, electrodes were attached to the skin of the leg, and in this condition the testee ran on a slope for 10 minutes, and the average value with respect to the upper portions of the inner and outer sides of the gastrocnemius was found, Mark ○ represents the numerical value measured immediately after the running was started, and mark · represents the numerical value measured seconds before the running was finished. As shown in FIG. 11, the degree of fatigue is low with high frequencies, and is high with low frequencies. B represents the case where no supporter was worn, and C represents the case where the supporter of the present invention was worn, and D represents the case where a conventional spats was worn, and E represents the case where a conventional tubular supporter for holding the central portion of the muscle was worn. As is clear from FIG. 11, by supporting the muscle without perpendicularly holding the central portion of the muscle, the stability of the muscle can be increased, and the fatigue resulting from a long-period exercise can be alleviated.

As described above, the wearing article of the present invention is composed of the easily-stretchable cloth 8 and the heavily-stretchable cloth piece or pieces 1, and the heavily-stretchable cloth piece 1 is provided so as to extend generally along the muscle fibers over the region from the tendon to the central portion of the muscle. Therefore, when this wearing article is worn on the human body in intimate contact with the body surface, the heavily-stretchable cloth piece 1 is quite strongly pressed against the body surface along the muscle fibers so as to support the region from the tendon to the central portion of the muscle. With this arrangement, the stability of the muscle is enhanced, and a good circulation of the blood and the lymph is obtained even when taking exercise for a long time, and muscle fatigue is alleviated. Therefore, with this taping function, a torn muscle, which would be caused by the fatigue due to an excessive use of the muscle of the calf and by an excessive stress on the muscle, can be prevented, and a remedy for such a torn muscle can be achieved, and besides the prevention of an injury by a blow against the lower leg, as well as a treatment for such an injury, can be provided.

Further, when wearing the wearing article of the present invention, the same effect as the taping treatment can be provided at the required portion extending along the central portion of the muscle, and besides upon wearing of the wearing article, even those who are not skillful in the taping treatment can have the tape support effect, and also the tightening pressure can be applied to part of the body.

Further, since the band-like heavily-stretchable cloth piece 1 which is strong and can apply a high tightening force is used, the motion of the muscle is suitably supported and controlled. Also, that portion except for the heavily-stretchable cloth piece 1 which portion covers and fits on the body surface is as elastic (stretchable) as that obtained with the prior art, and therefore excellent fitting, heat-retaining and protective properties are obtained.

Further, the one-piece cloth, having the heavily-stretchable portion and the easily-stretchable portion continuous with each other, is used, and therefore the silhouette upon wearing is smooth and beautiful, and no profile of the heavily-stretchable portion or the easily-stretchable portion appears on the outer surface of the wearing article.

What is claimed is:

1. A wearing article for wearing on a human body, said article including a supporter for wearing on a lower leg of the human body in pressed relation to a surface of the lower leg, the supporter comprising a heavily-stretchable potion in the shape of a band forming a portion of the supporter and an easily stretchable potion forming the remainder of the supporter, the heavily-stretchable portion being arranged to extend substantially longitudinally of the supporter along at least one lateral portion of a rear part of the supporter which is to be contacted with a rear surface of the lower leg, in such a manner that when the supporter is worn on the lower leg including a calf, the heavily-stretchable portion extends from an upper portion of the rear part of the supporter to a lower portion of the rear part of the supporter over at least one of the lateral portions of the calf without passing over either a dorsal or a ventral portion of the calf.

2. A wearing article according to claim 1, in which said heavily-stretchable potion is so provided so as to hold the Achilles' tendon, the soleus and the gastrocnemius.

3. A wearing article according to claim 1, in which two of said heavily-stretchable portions are provided in said supporter which extend, when in use from the Achilles' tendon toward the knee, one portion extending on one side portion of the gastrocnemius and the other portion extending on the opposite side portion of the gastrocnemius.

4. A wearing article to claim 2 or claim 3, in which said supporter has a tubular shape for fitting on the lower leg of said body.

5. A wearing article according to claim 4, in which said supporter is lined with said heavily-stretchable portion.

6. A wearing article according to claim 1, in which said easily-stretchable portion forms the exterior of the wearing article and has an interior, a portion of the interior being lined with said heavily-stretchable portion.

7. A wearing article according to claim 1, in which said heavily-stretchable portion is in the form of a band.

* * * * *